United States Patent
Harvey et al.

(10) Patent No.: US 10,335,465 B1
(45) Date of Patent: *Jul. 2, 2019

(54) MUTANT OPAA ENZYME WITH INCREASED CATALYTIC EFFICIENCY ON ORGANOPHOSPHORUS COMPOUND GP

(71) Applicant: U.S. Army Edgewood Chemical Biological Center, Washington, DC (US)

(72) Inventors: Steven P Harvey, Lutherville, MD (US); Melissa M Dixon, Abingdon, MD (US); Mark A Guelta, White Marsh, MD (US); Leslie R McMahon, Aberdeen, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/880,747

(22) Filed: Jan. 26, 2018

(51) Int. Cl.

| | |
|---|---|
| *C12N 9/16* | (2006.01) |
| *A61K 38/16* | (2006.01) |
| *A62D 7/00* | (2006.01) |
| *A61K 38/46* | (2006.01) |
| *A62D 3/02* | (2007.01) |
| *A62D 101/26* | (2007.01) |
| *A62D 101/02* | (2007.01) |

(52) U.S. Cl.
CPC .............. *A61K 38/465* (2013.01); *A62D 3/02* (2013.01); *A62D 2101/02* (2013.01); *A62D 2101/26* (2013.01)

(58) Field of Classification Search
CPC ........... C12N 9/16; C12N 9/14; A61K 38/465
See application file for complete search history.

(56) References Cited

U.S. PATENT DOCUMENTS

2016/0355792 A1* 12/2016 Pegan .................... A61K 31/46

* cited by examiner

*Primary Examiner* — Maryam Monshipouri
(74) *Attorney, Agent, or Firm* — Ulysses John Biffoni

(57) ABSTRACT

The invention is directed toward mutant, non-wild-type organophosphorus acid anhydrolase enzymes having three site mutations, methods of production, and methods of use to effectively degrade toxic organophosphorus compounds, most preferably GP (2,2'-dimethylcyclopentyl methylphosphonofluoridate).

8 Claims, 2 Drawing Sheets

Specification includes a Sequence Listing.

MUTANT OPAA ENZYME WITH INCREASED CATALYTIC EFFICIENCY ON ORGANOPHOSPHORUS COMPOUND GP

GOVERNMENT INTEREST

The invention described herein may be manufactured, used, and licensed by or for the United States Government.

FIELD OF THE INVENTION

The invention relates to novel enzymes that degrade one or more toxins. More specifically, the invention is related to mutants of organophosphorus acid anhydrolase capable of degrading chemical nerve agent GP and other organophosphorus compounds such as pesticides and chemical nerve agents.

BACKGROUND OF THE INVENTION

A number of organophosphorus ("OP") compounds used by the agriculture industry and the military are highly toxic and thus hazardous to human health and harmful to the environment. For example, acetylcholinesterase-inhibiting OP compounds comprise the active ingredient of pesticides such as paraoxon as well as G-type nerve agents such as Sarin and Soman, etc., developed for chemical warfare. Thus, it is very important to be able to detoxify such OP compounds and to decontaminate surfaces and substances contaminated with these compounds.

One approach being investigated as a potential solution to this problem is enzyme-mediated decontamination. For example, a class of enzymes known as organophosphorus acid ("OPA") anhydrolases ("OPAA") (EC 3.1.8.2) can catalyze the hydrolysis of a variety of OP compounds, including pesticides and fluorinated "G-type" nerve agents. These anhydrolases are mass produced via overexpression within recombinant organisms as described by U.S. Pat. No. 5,928,927 to Cheng et al., which is incorporated herein by reference.

One of the organophosphorus compounds, (2,2'-dimethylcydopentyl methylphosphonofluoridate, CAS registry number 453574-97-5), known as GP, is very toxic to humans. The median lethal dose ($LD_{50}$) for humans is estimated to be about 0.35 g/man when contact is through skin. The estimated $LCt_{50}$ for inhalation is estimated to be 70 mg min/$m^3$. No efficient and easily produced catalyst for GP degradation in the environment or in vivo is known. The native OPAA enzyme has been described to possess catalytic activity against various chemical nerve agents, but its activity against the particularly toxic agent GP (2,2'-dimethylcyclopentyl methylphosphonofluondate)(CAS registry number 453574-97-5)) is limited, and therefore, is marginally useful as a decontaminant or as a medical countermeasure for GP poisoning.

Efforts on producing organophosphorus acid anhydrolases for detoxifying organophosphorus compounds are well known in the art.

U.S. Pat. No. 5,928,927 to Cheng et al. teaches expression and composition comprising wild-type organophosphorus acid anhydrolases ("OPAA-2") from the bacteria strain *Alteromones* sp. JD6.5.

U.S. 2013/0071394 to Troyer et al. teaches compositions and combinations containing an organophosphorus bioscavenger and a hyaluronan-degrading enzyme that can be used to treat or prevent organophosphorus poisoning, including nerve agent poisoning and pesticide poisoning. However, the bioscavenger that Troyer utilizes is a wild-type OPAA.

Similar to '394, U.S. Pat. No. 8,920,824 to Rosenberg teaches treating humans exposed to sarin by inhalation of wild-type OPAA.

U.S. Pat. No. 9,017,982 to Shah et al. teaches a non-wild-type organophosphorus acid anhydrolases having an amino acid substitution at position 212, such that the mutated OPAA may degrade (ethyl {2-[bis(propan-2-yl)amino] ethyl}sulfanyl) (methyl)phosphinate and other V-agents. However, the mutation occurs only at position 212 and the reported increase in catalytic activity is on V-type agents.

U.S. 2015/0017186 to Troyer et al. teaches a composition comprising an organophosphorus bioscavenger and a hyaluronan-degrading enzyme, and its use thereof to treat organophosphorus poisoning.

U.S. 2016/0355792 to Pegan teaches a mutated OPAA having mutation at positions Y212F, V342L, and 1215Y for degrading VX and VR. However, the reported increase in catalytic activity is only for V-type agents. Therefore, new compounds and methods to effectively detoxify GP are needed.

SUMMARY OF THE INVENTION

The invention is directed towards a non-wild type organophosphorus acid anhydrolase protein ("OPAA") that includes a mutation at each of sequence positions 212, 342 and 215 of SEQ ID NO: 1. The wild-type amino acid Tyrosine (Y) at position 212 of SEQ ID NO: 1 is substituted with an amino acid selected from the group consisting of Glycine (G), Phenylalanine (F), Proline (P), Glutamine (Q), and Threonine (T). The wild-type amino acid Valine (V) at position 342 of SEQ ID NO: 1 is substituted with an amino acid selected from the group consisting of Leucine (L), Threonine (T), Cysteine (C), Arginine (R), and Histidine (H). The wild-type amino acid Isoleucine (I) at position 215 of SEQ ID NO: 1 is substituted with an amino acid selected from the group consisting of Leucine (L), Threonine (T), Cysteine (C), Arginine (R), Histidine (H), and Lysine (K). In one embodiment, the non-wild-type OPPA has the sequence of SEQ ID NO: 2, or a catalytically active fragment thereof, wherein Tyrosine (Y) at position 212 is replaced with Phenyalanine (F), Valine (V) at position 342 is replaced with Leucine (L), and Isoleucine (I) at position 215 is replaced with Lysine (K). The catalytic efficiency of this mutant on GP is approximately 4 times greater that than of the wild-type enzyme and to our knowledge, and has the highest value ever reported for an enzyme active on GP.

Also provided are kits and composition methods for catalytically degrading GP, and contacting GP with the inventive non-wild-type organophosphorus acid anhydrolase protein.

BRIEF DESCRIPTION OF THE DRAWINGS

The invention, together with other objects, features, aspects and advantages thereof will be more clearly understood from the following in conjunction with the accompanying drawings.

FIG. 1 illustrates the structure of nerve agent GP (2,2'-dimethylcyclopentyl methylphosphonofluoridate).

FIG. 2 illustrates the catalytic activity of wild-type OPAA, and OPAA mutants with substitutions at positions 212, 342 and 215 of SEQ ID NO: 1.

DETAILED DESCRIPTION OF THE INVENTION

Native OPAA was originally derived from the bacterium *Alteromonas* sp. JD6.5 and its gene has subsequently been cloned into *E. coli*. The native OPAA enzyme has been described to possess catalytic activity against various chemical nerve agents but relatively little activity against the particularly toxic and persistent agent GP was observed. Native OPAA has the amino acid sequence of:

```
                                                       (SEQ ID NO: 1)
  1 MNKLAVLYAE HIATLQKRTR EIIERENLDG VVFHSGQAKR QFLDDMYYPF

51 KVNPQFKAWL PVIDNPHCWI VANGTDKPKL IFYRPVDFWH KVPDEPNEYW

101 ADYFDIELLV KPDQVEKLLP YDKARFAYIG EYLEVAQALG FELMNPEPVM

151 NFYHYHRAYK TQYELACMRE ANKIAVQGHK AARDAFFQGK SEFEIQQAYL

201 LATQHSENDT PYGNIVALNE NCAILHYTHF DRVAPATHRS FLIDAGANFN

251 GYAADITRTY DFTGEGEFAE LVATMKQHQI ALCNQLAPGK LYGELHLDCH

301 QRVAQTLSDF NIVNLSADEI VAKGITSTFF PHGLGHHIGL QVHDVGGFMA

351 DEQGAHQEPP EGHPFLRCTR KIEANQVFTI EPGLYFIDSL LGPLAATDNN

401 QHINWDKVAE LKPFGGIRIE DNIIVHEDSL ENMTRELELD
```

The inventors have found that an OPAA having a mutation at each of positions 212, 342 and 215 of SEQ ID NO: 1 effectively catalyzes GP. The non-wild type organophosphorus acid anhydrolase protein preferably has the sequence of SEQ ID NO: 2, or a catalytically active fragment thereof. Specifically, the wild-type amino acid Tyrosine at position 212 is substituted with an amino acid selected from the group consisting of G, F, P. Q, and T. The wild-type amino acid valine at position 342 is substituted with an amino acid selected from the group consisting of L, T, C, R, and H. The wild-type amino acid isoleucine at position 215 is substituted with an amino acid selected from the group consisting of L, T, C, R, H and K. One particular combination of mutations, Y212F, V342L, and 1215K of SEQ ID NO: 1, whereby a tyrosine is replaced by a phenylalanine at position 212, valine is replaced by leucine at position 342, and isoleucine is replaced by lysine at position 215, catalyzes the degradation of GP with excellent efficiency as compared to the wild-type OPAA. This isolated mutant OPAA enzyme may be used for in vivo treatment of GP poisoning, or for the catalytic decontamination of GP from surfaces or in the environment.

In one embodiment, the inventive, isolated non-wild-type OPAA has a sequence of:

```
                                                  (SEQ ID NO: 2)
  1 MNKLAVLYAE HIATLQKRTR EIIERENLDG VVFHSGQAKR QFLDDMYYPF

51 KVNPQFKAWL PVIDNPHCWI VANGTDKPKL IFYRPVDFWH KVPDEPNEYW

101 ADYFDIELLV KPDQVEKLLP YDKARFAYIG EYLEVAQALG FELMNPEPVM

151 NFYHYHRAYK TQYELACMRE ANKIAVQGHK AARDAFFQGK SEFEIQQAYL

201 LATQHSENDT PFGNKVALNE NCAILHYTHF DRVAPATHRS FLIDAGANFN

251 GYAADITRTY DFTGEGEFAE LVATMKQHQI ALCNQLAPGK LYGELHLDCH

301 QRVAQTLSDF NIVNLSADEI VAKGITSTFF PHGLGHHIGL QLHDVGGFMA

351 DEQGAHQEPP EGHPFLRCTR KIEANQVFTI EPGLYFIDSL LGPLAATDNN

401 QHINWDKVAE LKPFGGIRIE DNIIVHEDSL ENMTRELELD
```

This preferred embodiment is referred to as OPAA FLK because of the amino acids at positions 212, 215, and 342. Alternatively, the non-wild-type OPAA may include 2, 3, 4, 5, 6, 7, 8, 9 or more non-wild-type amino acid residues located at positions other than positions 212, 342 and 215.

The non-wild-type OPAA may have additional non-wild-type amino acid substitutions, includes but not limited to a deletion, or an additional amino acid sequence contained within the non-wild-type OPAA sequence.

In some embodiments, the non-wild-type OPAA is a fragment of wild-type OPAA wherein the fragment includes sufficient residues of OPAA to enable the mutated OPAA to be as functional and active as a wild-type OPAA, yet catalytically breakdown GP at high efficiency. Preferably, the non-wild-type OPAA is of 440 amino acids in length.

Amino acids present in the non-wild-type OPAA include the common amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine as well as less common naturally occurring amino acids, modified amino acids or synthetic compounds, such as alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-sioleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylomithine, cyclopentyl alanine, cyclopropyl alanine, 3-sulfoalanine, 2,4-diaminobutanoic acid, diaminopropionic acid, 2,4-diaminobutyric acid, diphenyl alanine. NN-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, omithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, and 2-naphthylalanine.

Modifications and changes can be made in the structure of the inventive non-wild-type OPAA that are the subject of the application and still obtain a molecule having similar or improved characteristics as the Y212F-V342L-1215K mutated sequence (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like or improved properties. Optionally, a polypeptide is used that has less or more activity compared to the Y212F-V342L-1215K mutant sequence.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In making such changes, the substitution of amino acids whose hydropathic indices are preferably within ±2, more preferably within ±1, and most preferably within ±0.5.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are preferably within ±2, more preferably within ±1, and most preferably within ±0.5.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gin, His), (Asp: Glu, Cys, Ser), (Gin: Asn), (Glu: Asp), (Gly: ala), (His: Asn, Gin), (lie: Leu, Val), (Leu: Ile, Val), (Lys: Arg), (Met: Leu, Tyr), (Ser Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of polypeptides can include variants having about 50%, 69%, 70%, preferably 80%, 90%, and 95% sequence identity to the protein of SEQ ID NO: 1. More preferably, a tyrosine is replaced by a phenylalanine at position 212, valine is replaced by leucine at position 342, and isoleucine is replaced by leucine at position 215.

It is appreciated that amino acids are optionally L- or D-isomers. The inventive non-wild-type OPAA may include mixtures of L- and D-isomers.

Figure 1:
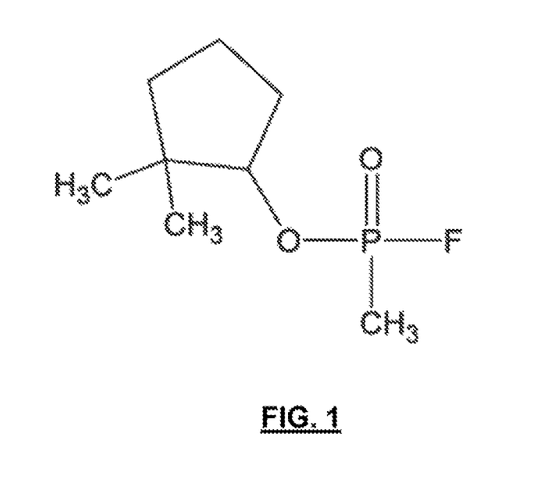
Figure 2:
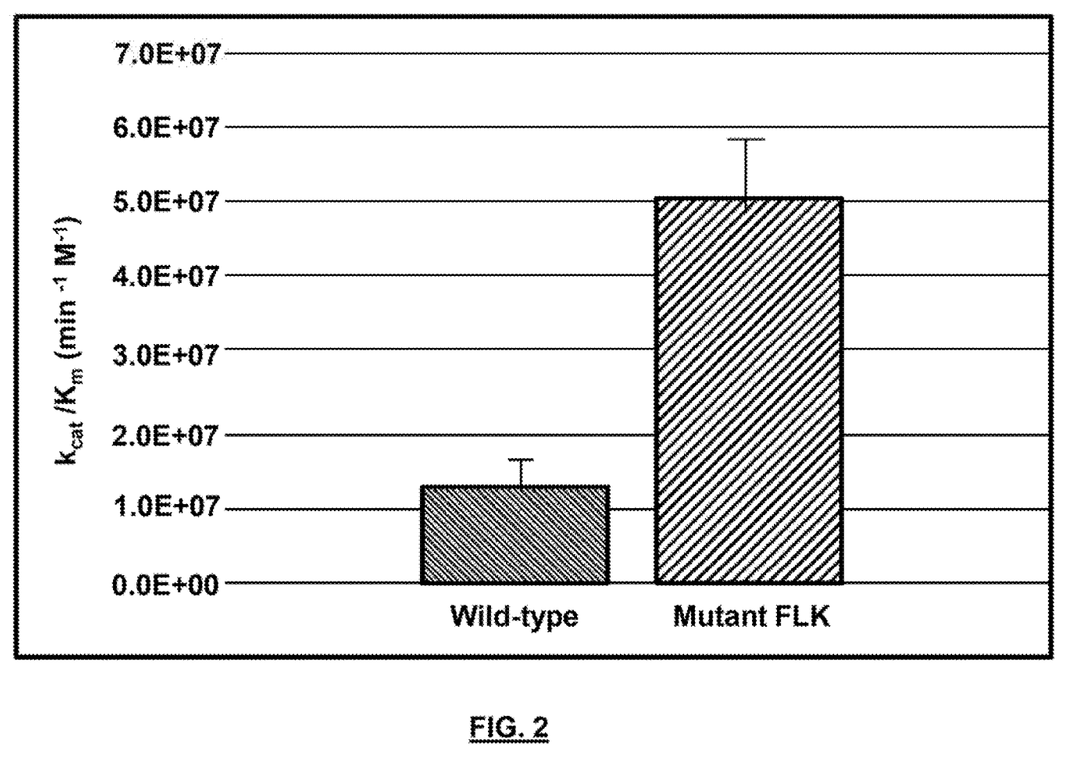

Without wish to be bound by theory, the OPAA has a substrate-binding site for chemicals. The substrate-binding site is composed of a small pocket, a large pocket, and a leaving group pocket. The large pocket is formed by Leu225, His226, His332, and Arg418. The leaving group pocket is composed of Tyr292 and Leu366. The small pocket is formed by residues Tyr212, Val342, His343, and Asp45 from the N-terminal domain of the opposite subunit in the dimer. All three pockets are in close proximity to the binuclear active site. It has been found for the present invention that modification for sites located within the small pockets of the OPAA, particularly 212 and 342, as well as site 215 in close proximity to the small pocket of SEQ ID NO: 1, imparts good binding and excellent catalytic activity of nerve-agents such as GP as shown in FIG. 2. The excellent catalytic activity may be due to the mutations narrow size of the small pocket significantly, such that GP is restricted to an orientation more favorable for catalysis of its P—F bonds.

Method of Production

The non-wild-type OPAA is obtained by any of various methods known in the art illustratively including isolation from a cell or organism, chemical synthesis, expression of a nucleic acid sequence, and partial hydrolysis of larger OPAA sequences. Chemical methods of peptide synthesis are known in the art and include solid phase peptide synthesis and solution phase peptide synthesis or by the method of Hackeng, T M, et al., *Proc Natl Acad Sci USA*, 1997; 94(15):7845-50 or those reviewed by Miranda, L P, *Peptide Science*, 2000, 55:217-26 and Kochendoerfer G, *Curr Opin Drug Discov Devel*. 2001; 4(2):205-14. In some embodiments, the polypeptide sequences are chemically synthesized by Fmoc synthesis.

Alternatively, synthesis and expression of the non-wild-type OPAA is illustratively accomplished from transcription of a nucleic acid sequence encoding a peptide of the invention, and translation of RNA transcribed from nucleic acid sequence, modifications thereof, or fragments thereof. Protein expression is optionally performed in a cell based system such as in *E. coli*, HeLa cells, or Chinese hamster ovary cells. It is appreciated that cell-free expression systems are similarly operable.

Further aspects of the present disclosure concern the purification, and in particular embodiments, the substantial purification, of a non-wild-type OPAA protein. The term "purified" or "isolated" as used herein, is intended to refer to a composition, isolatable from other components, wherein the non-wild-type OPAA is purified to any degree relative to its naturally-obtainable state. A purified non-wild-type OPAA, therefore, also refers to a non-wild-type OPAA free from the environment in which it may naturally occur.

Generally, "purified" or "isolated" will refer to a non-wild-type OPAA composition that has been subjected to fractionation to remove various other components, and which composition substantially retains its expressed biological activity. Where the term "substantially" purified is used, this designation will refer to a composition in which the protein or peptide forms the major component of the composition, such as constituting about 50% or more of the proteins in the composition.

Various methods for quantifying the degree of purification of a protein are known to those of skill in the art in light of the present disclosure as based on knowledge in the art. These include, for example, determining the specific activity of an active fraction, or assessing the number of peptides within a fraction by SDS/PAGE analysis. An illustrative method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in peptide purification will be well known to those of skill in the art. These include, for example, precipitation with ammonium sulfate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein.

Additional methods of protein isolation illustratively include column chromatography, affinity chromatography, gel electrophoresis, filtration, or other methods known in the art. In some embodiments, a non-wild-type OPAA is expressed with a tag operable for affinity purification. An illustrative tag is a 6× His tag. A 6× His tagged inventive protein is illustratively purified by Ni-NTA column chromatography or using an anti-6× His tag antibody fused to a solid support. (Geneway Biotech, San Diego, Calif.) Other tags and purification systems are similarly operable.

It is appreciated that an inventive protein is not tagged. In this embodiment and other embodiments purification may be achieved by methods known in the art illustratively including ion-exchange chromatography, affinity chromatography using antibodies directed to the peptide sequence of interest, precipitation with salt such as ammonium sulfate, streptomycin sulfate, or protamine sulfate, reverse chromatography, size exclusion chromatography such as gel exclusion chromatography, HPLC, immobilized metal chelate chromatography, or other methods known in the art. One of skill in the art may select the most appropriate isolation and purification techniques without departing from the scope of this invention.

There is no general requirement that the non-wild-type OPAA always be provided in its most purified state. It is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a protein can vary, sometimes significantly, with different conditions of SDS/PAGE (Capaldi et al., *Biochem. Biophys. Res. Comm.*, 76:425, 1977). It will, therefore, be appreciated that under differing electrophoresis conditions, the apparent molecular weights of purified or partially purified expression products may vary.

Non-wild-type OPAA proteins or peptides of this invention may optionally be characterized by measurements including, without limitation, western blot, marcomolecular mass determinations by biophysical determinations, SDS-PAGE/staining, HPLC and the like, antibody recognition assays, activity assays against various possible substrates illustratively including but not limited to GP (2,2'-dimethylcyclopentyl methylphosphonofluoridate), GD (O-Pinacolyl methylphosphonofluoridate), or GF (cyclohexyl methylphosphonofluoridate).

The nucleic acid encoding the non-wild-type OPAA of this invention can be any nucleic acid that functionally encodes the non-wild-type OPAA. To functionally encode the peptides (i.e., allow the nucleic acids to be expressed), the nucleic acid of this invention can include, for example, expression control sequences, such as an origin of replication, a promoter, an enhancer and necessary information processing sites, such as ribosome binding sites, RNA splice sites, polyadenylation sites and transcriptional terminator sequences.

The nucleic acid sequence encoding the non-wild-type OPAA of this invention is preferably cloned into the NcoI and EcoRI sites of a pSE420 expression vector. The cloned gene translates to a polypeptide that lacks the last 77 carboxyl-terminus amino acids of the OPAA enzyme. The truncation of the last 77 amino acids have been shown not to affect enzyme activity by Daczkowski, et al., *Biochemistry,* 2015, 54, 6423-6433, which is incorporated herein by reference. The OPAA enzyme with the Y212F-V342L-1215L mutations is constructed by site-directed mutagenesis.

Method of Use

It is further contemplated that a non-wild-type OPAA may be provided for pharmaceutical use. Pharmaceutical compositions optionally include effective amounts of non-wild-type OPAA, or derivative products, together with pharmaceutically acceptable diluents, preservatives, solubilizers, emulsifiers, adjuvants and/or carriers needed for administration. (See PCT 97101331 for an exemplary listing) The optimal pharmaceutical formulation for a desired biologically active agent will be determined by one skilled in the art depending upon the route of administration and desired dosage. Exemplary pharmaceutical compositions are disclosed in Remington's Pharmaceutical Sciences (Mack Publishing Co., 18th Ed., Easton, Pa., pgs. 1435-1712 (1990)). The pharmaceutical compositions of the present invention may be administered by oral and non-oral preparations (e.g., intramuscular, subcutaneous, transdermal, visceral, IV (intravenous), IP (intraperitoneal), intraarticular, placement in the ear, ICV (intracerebralventricular), intraarterial, intrathecal, intracapsular, intraorbital, injectable, pulmonary, nasal, rectal, and uterine-transmucosal preparations).

The non-wild-type OPAA may be delivered as naked polypeptide, in aqueous solution, in an emulsion, or in other suitable delivery composition. In some embodiments, the invention is delivered as a component of a pharmaceutical package. Alternatively, a protein (or multiple proteins) is present in an emulsion including one or more emulsification agents. In some embodiments, a non-wild-type OPAA is emulsified. Suitable emulsification agents illustratively include supramolecular biovectors (SMBV), nanoparticles such as described by Major, M. et al, *Biochim. Biophys. Acta,* 1997; 1327:32-40, De Migel, I, et al, *Pharm. Res.,* 2000; 17:817-824, U.S. Pat. Nos. 6,017,513, 7,097,849, 7,041,705, 6,979,456, 6,846,917, 6,663,861, 6,544,646, 6,541,030, 6,368,602, Castignolles, N., et al., *Vaccine,* 1996; 14:1353-1360, Prieur, E., et al, *Vaccine,* 1996; 14:511-520, Baudner B, et al, *Infect Immun,* 2002; 70:4785-4790; Liposomes such as described by El Guink et al., *Vaccine,* 1989; 7:147-151, and in U.S. Pat. No. 4,196,191; or other agents known in the art. Agents suitable for use are generally available from Sigma-Aldrich, St. Louis, Mo. The emulsification agent is optionally a dimethyl dioctadecyl-ammonium bromide. Optionally, the adjuvant is monophosphoryl lipid A.

Suitable pharmaceutically acceptable carriers facilitate administration of the non-wild-type OPAA are physiologically inert and/or nonharmful. Carriers may be selected by one of skill in the art. Exemplary carriers include sterile water or saline, lactose, sucrose, calcium phosphate, gelatin, dextran, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used.

The inventive composition may also contain conventional pharmaceutical ingredients, such as preservatives, or chemical stabilizers. Suitable ingredients operable herein include, for example, casamino acids, sucrose, gelatin, phenol red, N—Z amine, monopotassium diphosphate, lactose, lactalbumin hydrolysate, and dried milk.

Suitable methods of administration of a non-wild-type OPAA include, but are not limited to intramuscular, intravenous, intranasal, mucosal, oral, parenteral, intravaginal, transdermal, via aerosol delivery or by any route that produces the desired biological effect.

A non-wild-type OPAA protein of the invention may be packaged in a single dosage for administration by parenteral (i.e., intramuscular, intradermal or subcutaneous) or nasopharyngeal (i.e., intranasal) administration. The non-wild-type OPAA may also be delivered by inhalation. Alternatively, the non-wild-type OPAA is combined with a pharmaceutically acceptable carrier to facilitate administration. The carrier is usually water or a buffered saline, with or without a preservative. The non-wild-type OPAA may be lyophilized for resuspension at the time of administration or in solution.

The inventive non-wild-type OPAA may be microencapsulated to provide a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that may be considered. Examples of useful polymers illustratively include polycarbonates, polyesters, polyurethanes, polyorthoesters polyamides, poly (d,l-lactide-co-glycolide) (PLGA) and other biodegradable polymers.

The inventive non-wild-type OPAA may additionally contain stabilizers such as thimerosal (ethyl(2-mercaptobenzoate-S)mercury sodium salt) (Sigma Chemical Company, St. Louis, Mo.) or physiologically acceptable preservatives.

Further, an effective amount of a non-wild-type OPAA of the invention may be administered so that a human or other animal who are exposed to a toxin, illustratively GP, by administering an "effective amount" is of between about 0.05 to about 1000 μg/mL of the non-wild-type OPAA. A suitable dosage is about 1.0 mL of such an effective amount. Such a composition may be administered 1-3 times per day over a 1 day to 12 week period. However, suitable dosage adjustments may be made by the attending physician or veterinarian depending upon the age, sex, weight and general health of the subject. Such a composition may be administered parenterally, optionally intramuscularly or subcutaneously. However, the composition may also be formulated to be administered by any other suitable route, including orally or topically.

As used herein, the terms "subject" or "organism" are treated synonymously and are defined as any being that includes a gene, including a virus. A subject illustratively includes: a mammal including humans, non-human primates, horses, goats, cows, sheep, pigs, dogs, cats, and rodents; arthropods; single celled organisms illustratively bacteria; viruses; and cells.

In some embodiments, a process of decontaminating a surface is provided. Such processes include applying the non-wild-type OPAA to a surface is contaminated with one or more toxins, illustratively GP. Any delivery mechanism for decontaminating a surface with non-wild-type OPAA is operable including spraying, immersing, or other contact mechanism. The non-wild-type OPAA may be delivered in any form described above, preferably as an aqueous solution. For testing the contaminated surfaces, the non-wild-type OPAA is maintained in contact with the surface for a contact period sufficient to catalyze degradation, optionally complete degradation, of the toxin present on the surface.

In some embodiments, the invention provides regimens or kits comprising one or more of the following in a package or container: (1) a pharmacologically active composition comprising a pharmaceutically acceptable carrier and the inventive, non-wild-type OPAA or its variant, derivative or structural equivalent thereof; (2) an additional boosting agent; and (3) apparatus or applicator to administer the pharmaceutically active composition to the subject, such as a syringe, nebulizer, etc.

When a kit is supplied, the different components of the composition may be packaged in separate containers. If appropriate, and admixed immediately before use. Such packaging of the components separately may permit long-term storage without losing the active component's function.

The reagents included in the kits can be supplied in containers of any sort such at the life of the different components are preserved and are not adsorbed or altered by the materials of the container. For example, sealed glass ampules may contain lyophilized non-wild-type OPAA and variants, derivatives and structural equivalents thereof, or buffers that have been packaged under a neutral, non-reacting gas, such as nitrogen. Ampules may consist of any suitable material, such as glass, organic polymers, such polycarbonate, polystyrene, etc., ceramic, metal or any other material typically employed to hold similar regents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other container may have two compartments that are separated by a readily removable membrane that upon removal permits the components to be mixed. Removable membranes may be glass, plastic, rubber, etc.

Kits may also be supplied with instructional materials that describes a method for combining and administering the components. Instructions may be printed on paper or other substrate, and/or may be supplied as an electronic-readable medium, such as a floppy disc, CD-ROM, DVD-ROM, Zip disc, videotape, audiotape, flash memory device, wireless download, etc. Detailed instructions may not be physically associated with the kit; instead, a user may be directed to an internet web site specified by the manufacturer or distributer of the kit, or supplied as electronic mail.

EXPERIMENT

OPAA Expression Vector and Site-Directed Mutagenesis of the OPAA Gene

The gene encoding the OPAA enzyme was originally cloned from *Alteromonas* sp. JD6.5, as described. The present gene was modified by site-directed mutagenesis, lacks the last 77 carboxyl-terminus amino acids of the OPAA enzyme. This truncated gene was cloned into the NcoI and the EcoRI sites of the pSE420 expression vector of *E. coli*. The resulting mutant plasmids were introduced into *E. coli* BL21 (DE3) competent cells by electroporation and were grown to late log phase in 1 liter flasks without induction to produce enzyme. The complete coding regions for the mutant OPAA was sequenced by DNA2.0 (www.dna20.com).

Production and Purification of Engineered OPAAs

The engineered OPAA enzymes were prepared by a method similar to that described previously is U.S. Pat. No. 9,017,982, which is incorporated herein by reference. Briefly, an *E. coli* DH5a culture containing the OPAA containing the pSE420 plasmid was grown at 37° C. in 10 L of LB containing 0.1 mg/mL ampicillin and 0.1 mM $MnCl_2$. Cells were grown to mid-log phase (A600=0.5) and induced with 1 mM IPTG. After four hours of induction, the cells were harvested by centrifugation. After the centrifugation, proteins from the supernatant were precipitated in 65% ammonium sulfate. This pellet was resuspended in 13 mL of 10 mM bis-tris-propane, pH 8.0 with 0.1 mM $MnCl_2$ and passed through a size exclusion column. The active fractions were pooled and loaded on a 10 ml Q Sepharose column and eluted with a 0.2-0.6 M NaCl gradient. The active fractions from the Q Sepharose column were pooled, precipitated in 65% ammonium sulfate, resuspended in and dialyzed against 10 mM bis-tris-propane, pH 8.0 with 0.1 mM $MnCl_2$. The resulting protein migrated with apparent homogeneity on SDS-PAGE.

GP Enzymatic Assay

The enzymatic assay measured the concentration of free fluoride from the enzyme-catalyzed cleavage of the P—F bond of GP. GP samples were Chemical Agent Standard Analytical Reference Material (CASARM), obtained from Edgewood Chemical Biological Center Stocks, and were of the highest purity available, typically 99.9+/−5.4 weight % by oxidation-reduction titration, traceable to National Institute of Standards and Technology through 0.1 N iodine solution SRM 136e. The kinetic constants were determined by monitoring fluoride release with a fluoride electrode in 50 mM bis-tris-propane buffer, pH 8.0 and 0.1 mM $MnCl_2$ at 25° C. A wild-type sample and a sample containing mutations at positions 212, 215 and 342 were monitored for two minutes and activity was calculated.

Kinetic parameters were calculated using Biosoft EnzFitter© software (Biosoft.com). Activity data were generally collected at substrate concentrations ranging from ⅓ to three times the Km under conditions that consumed less than 10% of the substrate. At least five different substrate concentrations were used for each

TABLE 1

Kinetic parameters of wild-type (WT) and
FLK versons of the OPAA enzyme.

| Enzyme | $k_{cat}$ (min$^{-1}$) | $k_m$ (M$^{-1}$) | $k_{cat}/k_m$ (min$^{-1}$ M$^{-1}$) |
|---|---|---|---|
| WT | 7.91E+04 +/− 7.44E+03 | 6.12E+03 +/− 1.21E+03 | 1.29E+07 +/− 3.78E+06 |
| FLK | 1.74E+05 +/− 2.26E+04 | 3.44E+03 +/− 8.8E+02 | 5.06E+07 +/− 1.95E+07 |

The essential advantage of the OPAA FLK as compared to the wild-type OPAA enzyme lies in its 4 fold increased catalytic efficiency on GP. The $k_{cat}$ value of FLK mutant is about twice that of the wild-type, and the $K_m$ of the FLK mutant is about half that of the wild-type (lower $K_m$ indicating greater efficiency). As such, the $k_{cat}K_m$ value, or the catalytic efficiency is 4.0 times greater than wild-type.

As illustrated by FIG. 2, the mutated OPAA having three mutations has about 4 times greater catalytic efficiency as compared to the wild-type OPAA.

The foregoing description of the specific embodiments will so fully reveal the general nature of the embodiments herein that others may, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein may be practiced with modification within the spirit and scope of the appended claims.

The invention claimed is:

1. A mutant organophosphorus acid anhydrolase (OPAA) enzyme, wherein said mutant anhydrolase enzyme comprises the amino acid sequence of SEQ ID NO: 2.

2. A method of degrading GP (2,2'-dimethylcyclopentyl methylphosphonofluoridate), comprising contacting GP with a mutant organophosphorus acid anhydrolase, wherein said mutant hydrolase comprises the amino acid sequence of SEQ ID NO: 2.

3. The method of claim 2, wherein GP is in a subject.

4. The method of claim 3, wherein a pharmaceutical composition containing said anhydrolase is administered to said subject.

5. The method of claim 4, wherein a dosage of said anhydrolase is of between about 0.05 to about 1000 μg/mL of said anhydrolase.

6. The method of claim 4, wherein said pharmaceutical composition is administered by intravenous injection, subcutaneous injection or intraperitoneal injection.

7. A kit for degrading GP, comprising:

(a) a mutant organophosphorus acid anhydrolase, wherein said mutant anhydrolase comprises the amino acid sequence of SEQ ID NO: 2; and (b) a pharmaceutically-acceptable carrier.

8. The kit of claim 7, wherein said kit further includes at least one pharmaceutically-acceptable adjuvant or excipient.

* * * * *

SEQUENCE LISTING

<160> NUMBER OF SEQ ID NOS: 2

<210> SEQ ID NO 1
<211> LENGTH: 440
<212> TYPE: PRT
<213> ORGANISM: Unknown
<220> FEATURE:
<223> OTHER INFORMATION: Wild-Type Organophosphorus Acid Anhydrolase

<400> SEQUENCE: 1

```
Met Asn Lys Leu Ala Val Leu Tyr Ala Glu His Ile Ala Thr Leu Gln
1               5                   10                  15

Lys Arg Thr Arg Glu Ile Ile Glu Arg Glu Asn Leu Asp Gly Val Val
            20                  25                  30

Phe His Ser Gly Gln Ala Lys Arg Gln Phe Leu Asp Asp Met Tyr Tyr
        35                  40                  45

Pro Phe Lys Val Asn Pro Gln Phe Lys Ala Trp Leu Pro Val Ile Asp
    50                  55                  60

Asn Pro His Cys Trp Ile Val Ala Asn Gly Thr Asp Lys Pro Lys Leu
65                  70                  75                  80

Ile Phe Tyr Arg Pro Val Asp Phe Trp His Lys Val Pro Asp Glu Pro
                85                  90                  95

Asn Glu Tyr Trp Ala Asp Tyr Phe Asp Ile Glu Leu Leu Val Lys Pro
            100                 105                 110

Asp Gln Val Glu Lys Leu Leu Pro Tyr Asp Lys Ala Arg Phe Ala Tyr
        115                 120                 125

Ile Gly Glu Tyr Leu Glu Val Ala Gln Ala Leu Gly Phe Glu Leu Met
    130                 135                 140

Asn Pro Glu Pro Val Met Asn Phe Tyr His Tyr His Arg Ala Tyr Lys
145                 150                 155                 160

Thr Gln Tyr Glu Leu Ala Cys Met Arg Glu Ala Asn Lys Ile Ala Val
                165                 170                 175

Gln Gly His Lys Ala Ala Arg Asp Ala Phe Phe Gln Gly Lys Ser Glu
            180                 185                 190

Phe Glu Ile Gln Gln Ala Tyr Leu Leu Ala Thr Gln His Ser Glu Asn
        195                 200                 205

Asp Thr Pro Tyr Gly Asn Ile Val Ala Leu Asn Glu Asn Cys Ala Ile
    210                 215                 220

Leu His Tyr Thr His Phe Asp Arg Val Ala Pro Ala Thr His Arg Ser
225                 230                 235                 240
```

-continued

```
Phe Leu Ile Asp Ala Gly Ala Asn Phe Asn Gly Tyr Ala Ala Asp Ile
                245                 250                 255

Thr Arg Thr Tyr Asp Phe Thr Gly Glu Gly Phe Ala Glu Leu Val
            260                 265                 270

Ala Thr Met Lys Gln His Gln Ile Ala Leu Cys Asn Gln Leu Ala Pro
            275                 280                 285

Gly Lys Leu Tyr Gly Glu Leu His Leu Asp Cys His Gln Arg Val Ala
            290                 295                 300

Gln Thr Leu Ser Asp Phe Asn Ile Val Asn Leu Ser Ala Asp Glu Ile
305                 310                 315                 320

Val Ala Lys Gly Ile Thr Ser Thr Phe Phe Pro Gly His Leu Gly His
                325                 330                 335

His Ile Gly Leu Gln Val His Asp Val Gly Gly Phe Met Ala Asp Glu
                340                 345                 350

Gln Gly Ala His Gln Glu Pro Pro Glu Gly His Pro Phe Leu Arg Cys
                355                 360                 365

Thr Arg Lys Ile Glu Ala Asn Gln Val Phe Thr Ile Glu Pro Gly Leu
            370                 375                 380

Tyr Phe Ile Asp Ser Leu Leu Gly Pro Leu Ala Ala Thr Asp Asn Asn
385                 390                 395                 400

Gln His Ile Asn Trp Asp Lys Val Ala Glu Leu Lys Pro Phe Gly Gly
                405                 410                 415

Ile Arg Ile Glu Asp Asn Ile Ile Val His Glu Asp Ser Leu Glu Asn
                420                 425                 430

Met Thr Arg Glu Leu Glu Leu Asp
            435                 440

<210> SEQ ID NO 2
<211> LENGTH: 440
<212> TYPE: PRT
<213> ORGANISM: Unknown
<220> FEATURE:
<223> OTHER INFORMATION: Non-Wild-Type FLK Organophosphorus Acid
      Anhydrolase

<400> SEQUENCE: 2

Met Asn Lys Leu Ala Val Leu Tyr Ala Glu His Ile Ala Thr Leu Gln
1               5                   10                  15

Lys Arg Thr Arg Glu Ile Ile Glu Arg Glu Asn Leu Asp Gly Val Val
                20                  25                  30

Phe His Ser Gly Gln Ala Lys Arg Gln Phe Leu Asp Asp Met Tyr Tyr
            35                  40                  45

Pro Phe Lys Val Asn Pro Gln Phe Lys Ala Trp Leu Pro Val Ile Asp
        50                  55                  60

Asn Pro His Cys Trp Ile Val Ala Asn Gly Thr Asp Lys Pro Lys Leu
65                  70                  75                  80

Ile Phe Tyr Arg Pro Val Asp Phe Trp His Lys Val Pro Asp Glu Pro
                85                  90                  95

Asn Glu Tyr Trp Ala Asp Tyr Phe Asp Ile Glu Leu Leu Val Lys Pro
            100                 105                 110

Asp Gln Val Glu Lys Leu Leu Pro Tyr Asp Lys Ala Arg Phe Ala Tyr
            115                 120                 125

Ile Gly Glu Tyr Leu Glu Val Ala Gln Ala Leu Gly Phe Glu Leu Met
            130                 135                 140

Asn Pro Glu Pro Val Met Asn Phe Tyr His Tyr His Arg Ala Tyr Lys
```

```
145                 150                 155                 160
Thr Gln Tyr Glu Leu Ala Cys Met Arg Glu Ala Asn Lys Ile Ala Val
                165                 170                 175

Gln Gly His Lys Ala Ala Arg Asp Ala Phe Phe Gln Gly Lys Ser Glu
                180                 185                 190

Phe Glu Ile Gln Gln Ala Tyr Leu Leu Ala Thr Gln His Ser Glu Asn
                195                 200                 205

Asp Thr Pro Phe Gly Asn Lys Val Ala Leu Asn Glu Asn Cys Ala Ile
        210                 215                 220

Leu His Tyr Thr His Phe Asp Arg Val Ala Pro Ala Thr His Arg Ser
225                 230                 235                 240

Phe Leu Ile Asp Ala Gly Ala Asn Phe Asn Gly Tyr Ala Ala Asp Ile
                245                 250                 255

Thr Arg Thr Tyr Asp Phe Thr Gly Glu Gly Glu Phe Ala Glu Leu Val
                260                 265                 270

Ala Thr Met Lys Gln His Gln Ile Ala Leu Cys Asn Gln Leu Ala Pro
                275                 280                 285

Gly Lys Leu Tyr Gly Glu Leu His Leu Asp Cys His Gln Arg Val Ala
        290                 295                 300

Gln Thr Leu Ser Asp Phe Asn Ile Val Asn Leu Ser Ala Asp Glu Ile
305                 310                 315                 320

Val Ala Lys Gly Ile Thr Ser Thr Phe Pro Pro His Gly Leu Gly His
                325                 330                 335

His Ile Gly Leu Gln Leu His Asp Val Gly Gly Phe Met Ala Asp Glu
                340                 345                 350

Gln Gly Ala His Gln Glu Pro Pro Glu Gly His Pro Phe Leu Arg Cys
        355                 360                 365

Thr Arg Lys Ile Glu Ala Asn Gln Val Phe Thr Ile Glu Pro Gly Leu
        370                 375                 380

Tyr Phe Ile Asp Ser Leu Leu Gly Pro Leu Ala Ala Thr Asp Asn Asn
385                 390                 395                 400

Gln His Ile Asn Trp Asp Lys Val Ala Glu Leu Lys Pro Phe Gly Gly
                405                 410                 415

Ile Arg Ile Glu Asp Asn Ile Ile Val His Glu Asp Ser Leu Glu Asn
                420                 425                 430

Met Thr Arg Glu Leu Glu Leu Asp
        435                 440
```